(12) United States Patent
Miwa

(10) Patent No.: US 7,725,170 B2
(45) Date of Patent: May 25, 2010

(54) BREAST CARCINOMA DETECTOR

(75) Inventor: Mitsuharu Miwa, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 1681 days.

(21) Appl. No.: 10/471,015

(22) PCT Filed: Mar. 13, 2002

(86) PCT No.: PCT/JP02/02370

§ 371 (c)(1),
(2), (4) Date: Sep. 8, 2003

(87) PCT Pub. No.: WO02/078547

PCT Pub. Date: Oct. 10, 2002

(65) Prior Publication Data

US 2004/0097810 A1 May 20, 2004

(30) Foreign Application Priority Data

Mar. 14, 2001 (JP) ............................. 2001-072510

(51) Int. Cl.
*A61B 6/00* (2006.01)
(52) U.S. Cl. .................... 600/476; 600/473; 600/310
(58) Field of Classification Search ......... 600/309–344, 600/407, 408, 431, 473–480
See application file for complete search history.

(56) References Cited

U.S. PATENT DOCUMENTS

| 4,212,306 | A | | 7/1980 | Mahmud |
| 4,945,239 | A | | 7/1990 | Wist et al. |
| 5,139,025 | A | | 8/1992 | Lewis et al. |
| 5,692,511 | A | * | 12/1997 | Grable ....................... 600/425 |
| 5,722,407 | A | | 3/1998 | Klingenbeck-Regn et al. ....................... 128/653.1 |
| 5,730,133 | A | | 3/1998 | Godik |

(Continued)

FOREIGN PATENT DOCUMENTS

DE 44 45 214 6/1996

(Continued)

*Primary Examiner*—Long V Le
*Assistant Examiner*—Sanjay Cattungal
(74) *Attorney, Agent, or Firm*—Drinker Biddle & Reath LLP

(57) ABSTRACT

The breast cancer detector of the invention comprising a transparent breast pressing member 1 having a pressing face 4 which is pressed to a breast of a subject that makes it possible to observe the breast pressed to the body from the opposite face to the pressing face 4, a light source means 2 for irradiating light of a designated wavelength with respect to the breast in an area to which the pressing face 4 is pressed and an image pickup means 3 sensitive to light from the breast derived from irradiated light of the light source means 2 and obtaining the breast image through the breast pressing member 1, wherein breast cancer is detected from the breast image obtained by the image pickup means. Therefore, the breast is pressed to the body by using the breast pressing member 1 to keep the breast thin, thus making it possible to irradiate uniformly the light emitted from the light source 2 to an area of the breast to which the pressing face 4 is pressed. The light from the breast derived from the irradiated light is obtained from the image pickup means 3 to detect breast cancer in the breast from the thus-obtained image.

9 Claims, 6 Drawing Sheets

U.S. PATENT DOCUMENTS

| | | | |
|---|---|---|---|
| 5,825,031 A * | 10/1998 | Wong et al. | 250/363.03 |
| 5,899,865 A * | 5/1999 | Chance | 600/473 |
| 5,952,664 A | 9/1999 | Wake et al. | |
| 6,029,077 A * | 2/2000 | Wake et al. | 600/407 |
| 6,091,983 A * | 7/2000 | Alfano et al. | 600/431 |
| 6,205,353 B1 * | 3/2001 | Alfano et al. | 600/476 |
| 6,254,614 B1 * | 7/2001 | Jesseph | 606/130 |
| 6,292,682 B1 * | 9/2001 | Kruger | 600/407 |
| 6,345,194 B1 * | 2/2002 | Nelson et al. | 600/425 |
| 6,824,648 B2 * | 11/2004 | Edwards et al. | 162/111 |
| 7,103,205 B2 * | 9/2006 | Wang et al. | 382/132 |
| 2001/0031934 A1 * | 10/2001 | Sarvazyan et al. | 600/587 |
| 2002/0035327 A1 * | 3/2002 | Kruger | 600/476 |
| 2003/0073930 A1 * | 4/2003 | Morrissey et al. | 600/573 |
| 2003/0090267 A1 * | 5/2003 | Rubashov | 324/318 |
| 2003/0176793 A1 * | 9/2003 | Wake et al. | 600/473 |
| 2004/0030227 A1 * | 2/2004 | Littrup et al. | 600/300 |
| 2004/0034307 A1 * | 2/2004 | Johnson et al. | 600/459 |
| 2005/0171430 A1 * | 8/2005 | Zhang et al. | 600/437 |
| 2005/0197583 A1 * | 9/2005 | Chance | 600/476 |

FOREIGN PATENT DOCUMENTS

| | | |
|---|---|---|
| JP | 05-223738 | 8/1993 |
| JP | 07-163571 | 6/1995 |
| JP | 09-309845 | 12/1997 |
| WO | WO 95/02987 | 2/1995 |
| WO | WO 97/36539 | 10/1997 |
| WO | WO 98/42248 | 10/1998 |
| WO | WO 00/37924 | 6/2000 |

* cited by examiner

BREAST CARCINOMA DETECTOR

TECHNICAL FIELD

The present invention relates to a technology for detecting breast cancer tissues in the living body in a non-invasive fashion by means of light.

BACKGROUND ART

At present, X-ray mammography has been commonly used as a non-invasive breast cancer detector. This detector detects breast cancer tissues by holding a breast between two plates vertically or horizontally to image it radiographically in the direction of the plates.

DISCLOSURE OF THE INVENTION

Therefore, the equipment has a problem of inflicting pain on a subject in the process of pressing a breast with the plates. It also has a problem of difficulty in holding a breast between the plates when the breast is too large or too small. Further, there is a concern about X-ray irradiation which may affect the breast or may relate to the occurrence of breast cancer.

JP-A No.5-223738 disclosed technology in which excitation light is irradiated from a laser light source to a sample containing a fluorescent source to obtain a fluorescent image by the image pickup means located away from the sample.

This invention is to eliminate the above problems and concerns and to provide a breast cancer detector capable of detecting breast cancer safely, easily and without inflicting pain on a subject.

The invention relates to a breast cancer detector, the breast cancer detector comprising a transparent breast pressing member having a pressing face which is pressed to a breast of a subject, that makes it possible to observe a breast pressed to the body from the opposite face to the pressing face, a light source means for irradiating light of a designated wavelength at least to a part of a breast in an area to which the pressing face is pressed and an image pickup means sensitive to light from a breast derived from irradiated light of the light source means and obtaining a breast image through the breast pressing member, wherein breast cancer is detected from the breast image obtained by the image pickup means.

Such structure of the breast cancer detector of the invention makes it possible to press a breast to the body with the breast pressing member, thus thinning the thickness of the breast vertical to the pressing face. It is possible to irradiate light down to the depth of a breast by irradiating the light of a designated wavelength from the light source to an area of the breast to which the pressing face is pressed in a state where the breast is kept thin. Further, light from the breast derived from the irradiated light, for example, reflected light from breast cancer tissues is obtained by the image pickup means at the place opposite to the pressing face of the breast pressing member, thus detecting breast cancer in the breast from the image.

In this instance, the pressing face of the breast pressing member is provided with a reference mark at which the nipple is placed, and when the reference mark is superimposed on the breast image obtained from the image pickup means, an exact site of breast cancer can be identified on the basis of the reference mark.

In addition, if the light source means is a ring-shaped light source mounted on the pressing face side of the breast pressing member in such a manner to surround the pressing face, it can irradiate light according to the configuration of the breast but will not interfere with observation to be made by the image pickup means at the place opposite to the pressing face.

Further, the light source means is a light source for irradiating light to the inside of a transparent member consisting of the breast pressing member, and able to irradiate light to an area of the breast contacting with the pressing face, when the light from the light source means is irradiated from the place contacting with the pressing face to the breast.

The light source means is also a light source for irradiating light of a wavelength whose absorption coefficient at breast tissues is different from the absorption coefficient at breast cancer tissues, and the image pickup means is able to easily differentiate the breast cancer tissues from breast tissues by referring to the breast image obtained when reflected, scattered or diffused light from at least either breast tissues or breast cancer tissues being imaged.

Further, the light source means is a light source for irradiating light of the wavelength of exciting a fluorescent contrast medium which selectively aggregates at breast cancer tissues and the image pickup means is sensitive to the fluorescent wavelength of the fluorescent contrast medium. When the image pickup means is so structured to obtain the fluorescent image of a breast of a subject to whom the fluorescent contrast medium is administered, the fluorescent image of the fluorescent contrast medium aggregated at breast cancer tissues can be obtained by the image pickup means by injecting the fluorescent contrast medium to the subject and irradiating light of excitation wavelength to the breast.

The breast pressing member may be provided with a filter that can permit light having a fluorescent wavelength of a fluorescent contrast medium to be transmitted selectively. In this case, the image pickup means can provide a sharper fluorescent image.

The light source means is also a light source for irradiating light of a wavelength that can excite the fluorescent contrast medium which will selectively aggregate at breast cancer tissues, and the image pickup means is sensitive to excitation light wavelength of the fluorescent contrast medium and may be structured to obtain an excitation light image of a breast of a subject to whom a fluorescent contrast medium is administered.

In this instance, the fluorescent contrast medium is injected in advance into the subject and then light having an excitation wavelength is irradiated to the breast. The excitation light which is irradiated to the breast will then excite the fluorescent contrast medium that aggregates at breast cancer tissues and produces fluorescence, whereas it will be reflected, scattered or diffused at healthy breast tissues. Since, of lights derived from the excitation light, the reflected, scattered and diffused lights are identical to the excitation light in the wavelength, these lights are obtained as an excitation light image by the image pickup means sensitive to the excitation light wavelength. Apart of the excitation light image is detected as healthy breast tissues and a part devoid of the excitation light image is detected as breast cancer tissues.

Further, the breast pressing member may be provided with a filter that blocks selective light of a fluorescent wavelength of a fluorescent contrast medium. In this case, the image pickup means can provide a sharper excitation light image.

The breast pressing member may also be provided with some reflecting means that permit the light of a wavelength projected from the light source means to selectively reflect from the pressing face to the breast side of a subject. In this case, when light is irradiated from the light source means to the breast pressing member, light reflected selectively by the reflecting means is irradiated from the pressing face to the breast, thus making it possible to irradiate light to an area of the breast contacting with the pressing face.

BEST MODE FOR CARRYING OUT THE INVENTION

Hereinafter, an explanation will be made about the embodiments of the invention by referring to the attached drawings. The same symbols are given to the same elements and description thereof is omitted.

Figure 1:
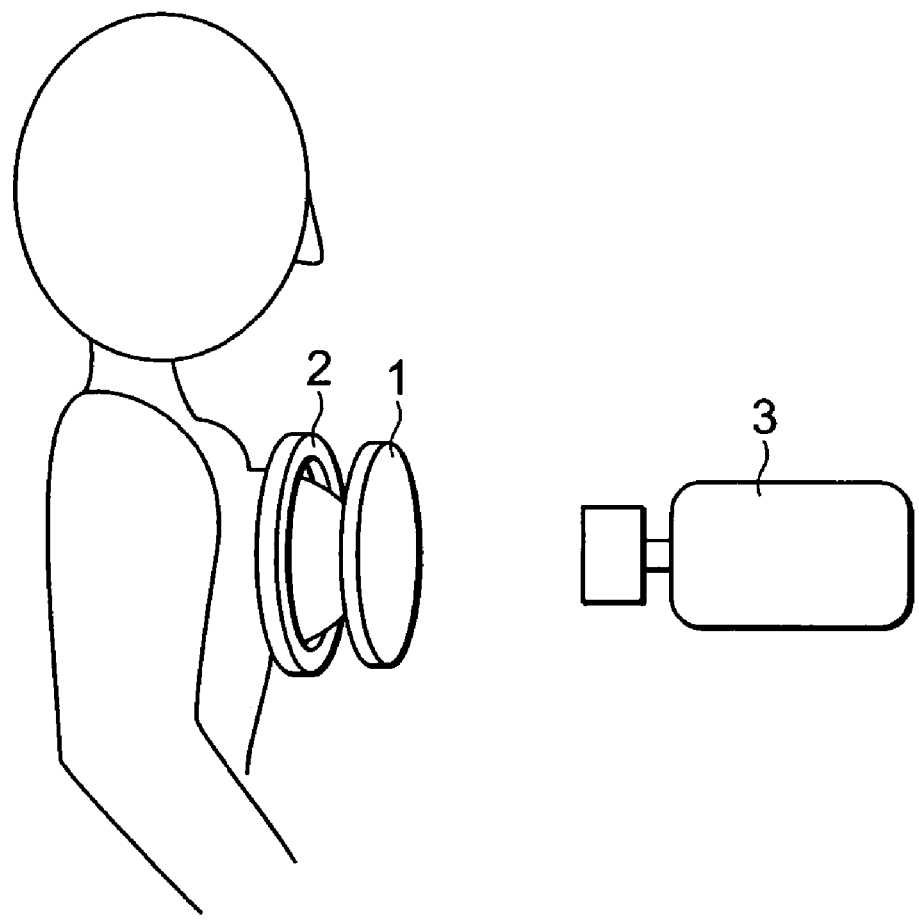
FIG. 1 is a schematic block diagram of an embodiment of the invention.
Figure 2:
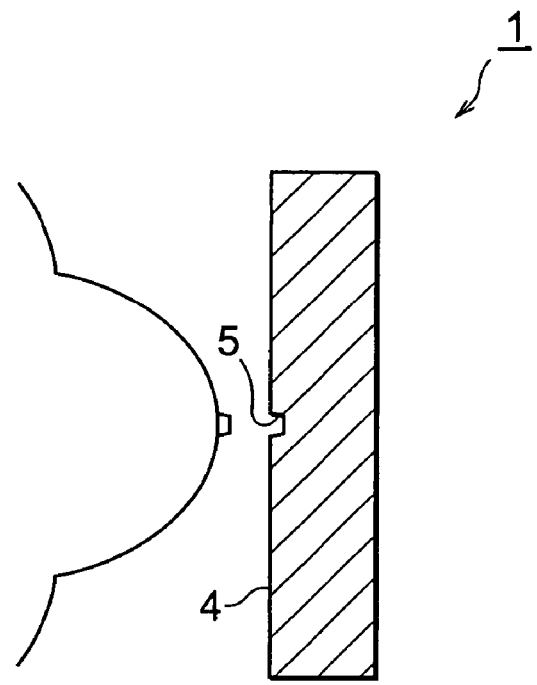
FIG. 2 is a cross-sectional view of the breast pressing member of the first embodiment when viewed from the side of the breast.
Figure 3:
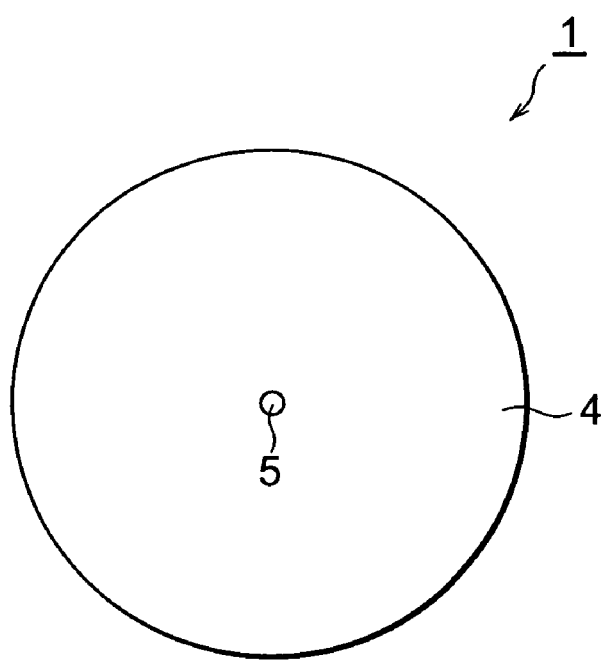
FIG. 3 is a front view of the breast pressing member of the first embodiment when viewed from the front of the breast.

FIG. 1 is a schematic block diagram showing the breast cancer detector given in the first embodiment of the invention. The breast pressing member 1 is of a disk shape. FIG. 2 gives a view from the side of the breast and FIG. 3 gives a view from the front of the breast. Providing a vertical scanning to the pressing face 4 of the breast pressing member 1 thins the breast to such an extent that will not inflict pain on a subject. The pressing face 4 is provided with a recess as the reference mark 5, and placing the nipple to the recess always equalizes the relative position of the breast to the breast pressing member 1.

The image pickup means 3 is a CCD camera, located at a place opposite to the breast with respect to the breast pressing member 1, and mounted through the breast pressing member 1 so as to obtain a breast image. The image obtained by the image pickup means 3 is displayed on a monitor, etc., or recorded as data.

The light source means 2 in which a laser diode is arranged in a ring shape is positioned in a manner to surround the breast. The light a irradiated from light source 2 to the breast is a light of wavelength easily absorbed into breast tissues rather than into breast cancer tissues. The wavelength of irradiated light used in the present embodiment should be preferably in a range of 600 nm to 1 µm, when consideration is given to the effects of scatter and diffusion within the breast, however any wavelength is used, as long as absorption coefficient of breast cancer tissues is different from that of breast cancer tissues.

Thus, light reflected, scattered or diffused only at breast cancer tissues is obtained from a breast by the image pickup means 3 through the transparent breast pressing member 1. The thus-obtained image is displayed on a monitor, etc., to detect breast cancer. Where breast cancer is detected, the position, size, etc., of the breast cancer are identified on the basis of the reference mark 5 on the pressing face 4 superimposed on the obtained image.

Where the wavelength of irradiated light is more easily absorbed into breast cancer tissues than into breast tissues and the light reflected, scattered or diffused at breast tissues is obtained by the image pickup means 3, a range in which the irradiated light is absorbed can be detected, thus making it possible to confirm the presence or absence of breast cancer and identify the position, size, etc., of the cancer, if detected.

Then, the following shows an aspect of the second embodiment of the breast cancer detector according to the present invention. The breast pressing member 1, light source unit 2 and image pickup device 3 are positioned similarly as given in the first embodiment.

Figure 4:
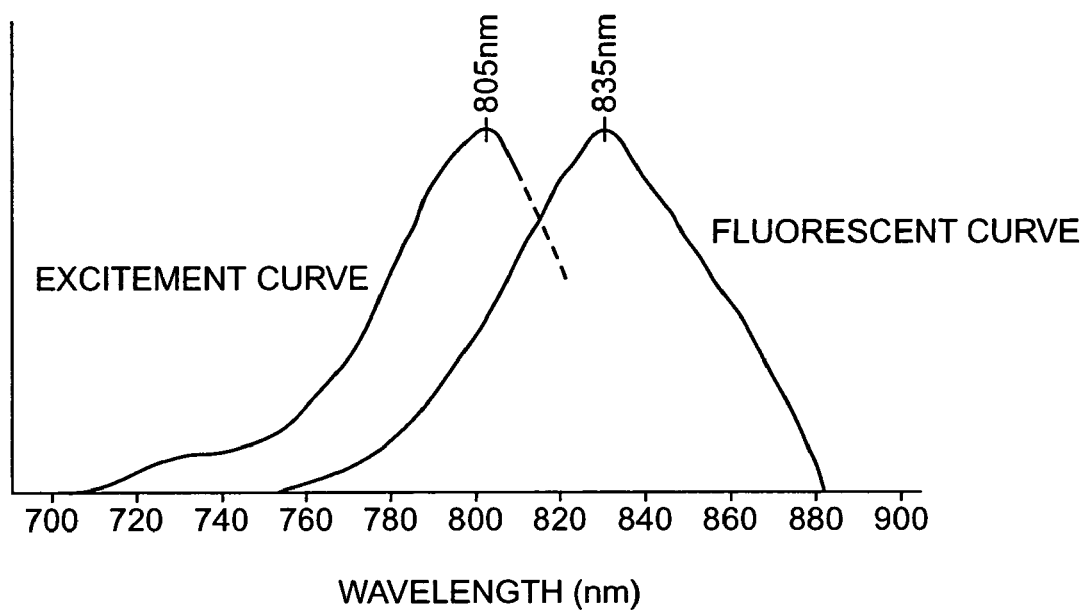
FIG. 4 is a view showing fluorescent properties of the fluorescent contrast medium used in the second through fourth embodiments.

In the present embodiment the fluorescent contrast medium (Cardio Green) that has such excitement and fluorescent properties as shown in FIG. 4 is used. Namely, this fluorescent contrast medium is characterized in that it is excited by light having a wavelength of around 805 nm and emits fluorescence having a wavelength of around 835 nm.

Figure 5:
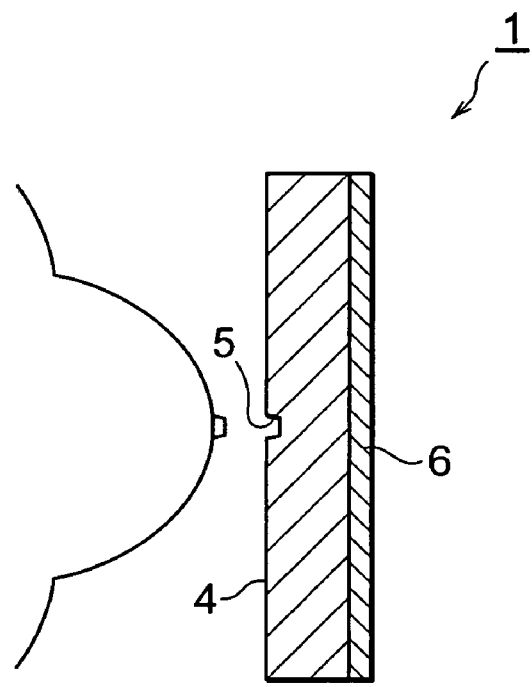
FIG. 5 is a cross-sectional view of the breast pressing member of the second embodiment when viewed from the side of the breast.

FIG. 5 shows a view of the breast pressing member 1 when viewed from the side of a breast. This breast pressing member 1 is the same as that given in the first embodiment, except that the surface opposite to the pressing face 4 is covered with a filter 6 which permits only light having a fluorescent wavelength (around 835 nm) of a fluorescent contrast medium to be transmitted.

Therefore, when a fluorescent contrast medium is injected into a subject to cause a selective aggregation at breast cancer tissues and irradiate excitation light having a central wavelength of 805 nm to the breast, the fluorescent contrast medium at breast cancer tissues emits fluorescence having a wavelength of around 835 mm. Fluorescence of the fluorescent contrast medium is obtained through the breast pressing member 1 by the image pickup means 3 sensitive to the fluorescent wavelength. The fluorescent image is observed on a monitor, etc., to confirm the presence or absence of breast cancer and identify the position, size, etc., of the cancer.

An aspect of the third embodiment of the breast cancer detector of the invention is also shown below. The breast pressing member 1, light source unit 2 and image pickup device 3 are positioned similarly as given in the first and second embodiments.

The present embodiment is different from the second embodiment in that the image pickup device 3 is sensitive to an excitation light wavelength, the filter 6 attached to the breast pressing member 1 blocks only a fluorescent wavelength of a fluorescent contrast medium.

The same fluorescent contrast medium as used in the second embodiment is injected in advance into a subject, and then light having a wavelength (805 nm) that excites the fluorescent contrast medium is irradiated from the light source 2 to the breast. After irradiated by excitation light, breast cancer tissues at which the fluorescent contrast medium aggregates emit light of a fluorescent wavelength (835 nm) and healthy breast tissues emit reflected, scattered and diffused light, the wavelength of which is similar to the excitation light.

Since fluorescence is blocked by the filter 6 mounted on the breast pressing member 1 and the image pickup device 3 is sensitive to light having an excitation wavelength, an excitation light image derived from reflected, scattered or diffused light is obtained by the image pickup device 3. This excitation light image is confirmed by a monitor or others, and an area of the excitation light image is detected as healthy breast tissues while an area devoid of the excitation light image is detected as breast cancer tissues. In some instances, the light image can be treated similarly as carried out in the fluorescent image of the second embodiment by inverting the output of the monitor, etc.

Also, given herewith is the fourth embodiment of the breast cancer detector of the invention. Positioning for the breast pressing member 1 and image pickup device 3 with respect to a breast are as positioned in the first through third embodiments. The same fluorescent contrast medium as used in the second and third embodiments is used.

Figure 6:
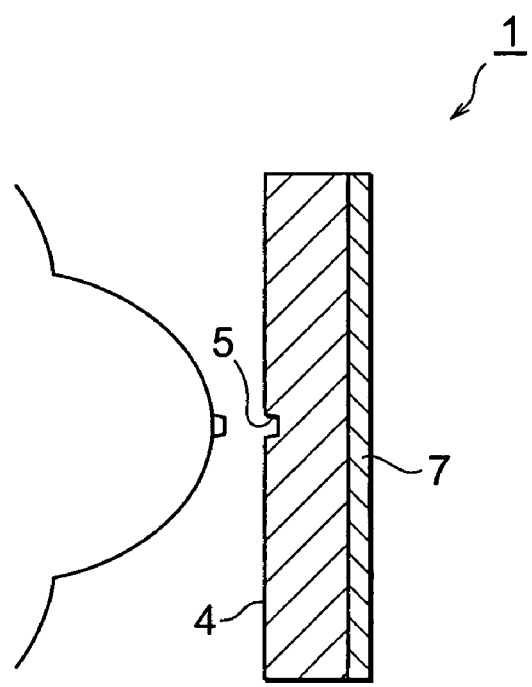
FIG. 6 is a cross-sectional view of the breast pressing member of the fourth embodiment when viewed from the side of the breast.

FIG. 6 shows a view of the breast pressing member 1 consisting of the breast cancer detector of the present embodiment when viewed from the side of the breast. As apparent in the drawing, an area opposite to the pressing face 4 is covered with the reflection membrane 7. This reflection membrane 7 is provided with properties that will reflect light of a wavelength (805 nm) which excites the fluorescent contrast medium and will permit light of a fluorescent wavelength (835 nm) to be transmitted.

The excitation light from the light source 2 is irradiated into the breast pressing member 1, and reflected to the pressing face 4 through the reflection membrane 7. Namely, the excitation light is irradiated to the breast through the pressing face 4.

The excitation light irradiated to the breast excites the fluorescent contrast medium which aggregates at breast cancer tissues of a subject, and produces fluorescence. Only the fluorescence can be obtained through the reflection membrane by the image pickup means 3, and displayed on a monitor, etc., to confirm the presence or absence of breast cancer and identify the position, size, etc., of the cancer.

Further, this invention shall not be limited to the above-mentioned embodiments but can be available in various modifications.

Figure 7:
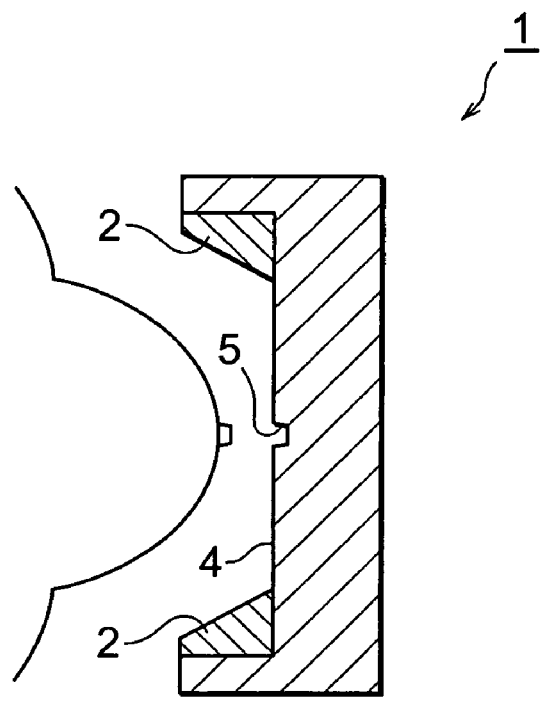
FIG. 7 is a cross-sectional view of the light source-mounted breast pressing member of the modified example 1 when viewed from the side of the breast.
Figure 8:
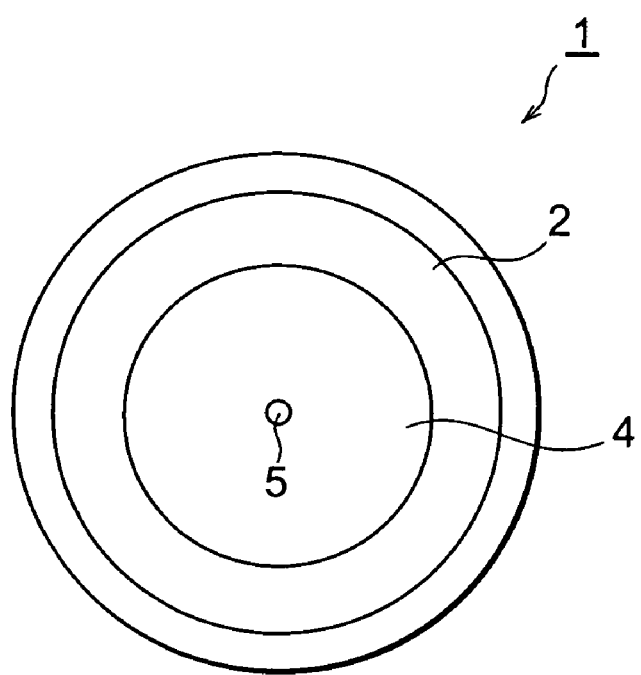
FIG. 8 is a front view of the light source-mounted breast pressing member of the modified example 1 when viewed from the front of the breast.
Figure 9:
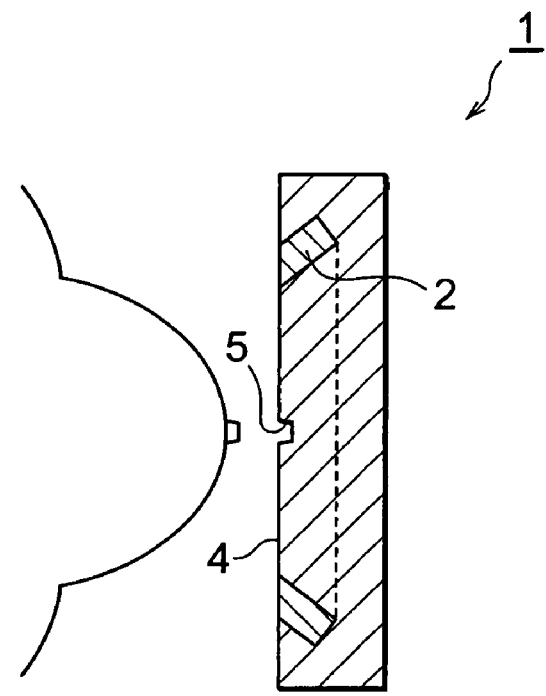
FIG. 9 is a cross-sectional view of the light-source mounted breast pressing member of the modified example 2 when viewed from the side of the breast.
Figure 10:
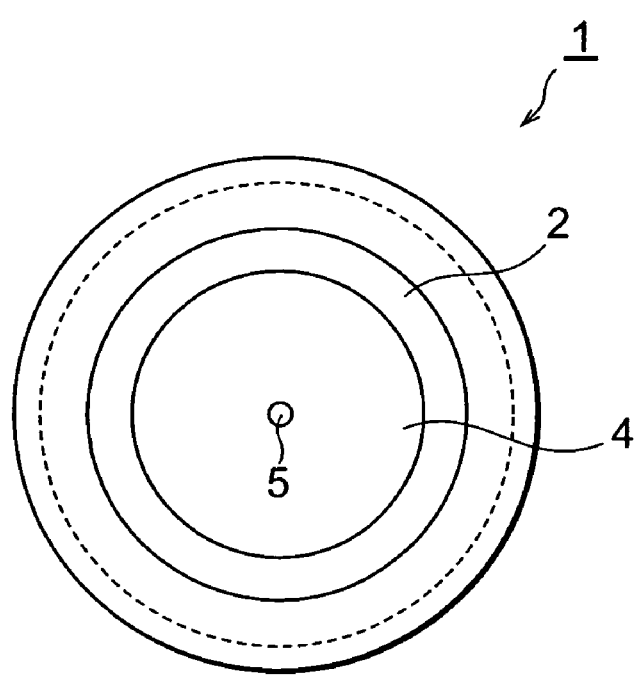
FIG. 10 is a front view of the light source mounted breast pressing member of the modified example 2 when viewed from the front of the breast.

For example, the light source 2 may be combined into the breast pressing member 1. FIG. 7 shows a view of the modified example 1 when viewed from the side of the breast, and FIG. 8 shows another view of the modified example 1 when viewed from the front of the breast. Further, FIG. 9 shows a view of the modified example 2 when viewed from the side of the breast, and FIG. 10 shows another view of the modified example 2 when viewed from the front of the breast. The above modified examples act in a similar way as those in which the breast pressing member 1 is separated from the light source 2.

Further, the breast pressing member 1 is not necessarily in a disk shape but may be in an oval shape or in a square shape. The material may be transparent or colored as long as it can pass the light from the light source or breast. In addition, the reference mark 5 is not necessarily a recess but may be anything that can specify the reference position.

A desirable shape of the pressing face 4 is a plane or a curved surface, with consideration given to the breast configuration or possible deformation, and an area to which the pressing face 4 is pressed may cover the whole of a breast or a part of a breast, for example, an area covering only a part of the breast around the armpit where breast cancer often develops.

The light source means may be a light-emitting diode and the image pickup means may be an II (image intensifier).

INDUSTRIAL APPLICABILITY

This invention can be used in a device for detecting breast cancer tissues in the living body.

The invention claimed is:

1. A breast cancer detector comprising:
a transparent breast pressing member having a pressing face configured to be pressed against a nipple of a breast of a subject to observe the breast pressed to the body from the opposite face to said pressing face;
a light source configured to irradiate light of a designated wavelength at least to a part of the breast in an area to which said pressing face is pressed; and
an image pickup device sensitive to light from the breast derived from irradiated light of said light source and obtaining the breast image through said breast pressing member,
wherein said light source is a ring-shaped light source mounted on said pressing face side of said breast pressing member, and configured to surround the breast of the subject when the pressing member is pressed against the nipple of the breast of the subject.

2. The breast cancer detector according to claim 1,
wherein said pressing face of said breast pressing member is provided with a reference mark at which the nipple is placed and said reference mark is superimposed on the breast image obtained by said image pickup device.

3. The breast cancer detector according to claim 1,
wherein said light source is a light source for irradiating light into the transparent member consisting of said breast pressing member, and so structured that light is irradiated from the surface contacting with said pressing face to the breast.

4. The breast cancer detector according to claim 1,
wherein said light source is a light source for irradiating light of a wavelength whose absorption coefficient at breast tissues is different from the absorption coefficient at breast cancer tissues, and said image pickup device is able to image reflected, scattered or diffused light from at least either breast tissues or breast cancer tissues.

5. The breast cancer detector according to claim 1,
wherein said light source is a light source for irradiating light having a wavelength of exciting a fluorescent contrast medium that will make a selective aggregation at breast cancer tissues, and said image pickup device is sensitive to a fluorescent wavelength of said fluorescent contrast medium and so structured to obtain the fluorescent image of the breast of a subject to whom said fluorescent contrast medium is administered.

6. The breast cancer detector according to claim 5,
wherein said breast pressing member is provided with a filter that can permit light having a fluorescent wavelength of said fluorescent contrast medium to be transmitted selectively.

7. The breast cancer detector according to claim 1,
wherein said light source is a light source for irradiating light having a wavelength of exciting a fluorescent contrast medium which will aggregate selectively at breast cancer tissues, and said image pickup device is sensitive to a light wavelength which excites said fluorescent contrast medium and so structured to obtain the excitation light image of a breast of a subject to whom said fluorescent contrast medium is administered.

8. The breast cancer detector according to claim 7,
wherein said breast pressing member is provided with a filter that selectively blocks the light of fluorescent wavelength of said fluorescent contrast medium.

9. The breast cancer detector according to claim 1,
wherein said breast pressing member is provided with a reflecting device that permits light of the wavelength projected from said light source to reflect selectively from said pressing face to the breast side of a subject.

* * * * *